(12) United States Patent
Oldham et al.

(10) Patent No.: US 6,970,240 B2
(45) Date of Patent: Nov. 29, 2005

(54) COMBINATION READER

(75) Inventors: Mark F. Oldham, Los Gatos, CA (US); Howard G. King, Berkeley, CA (US); Douwe D. Haga, Redwood City, CA (US); Tracy L. Ferea, Mountain View, CA (US)

(73) Assignee: Applera Corporation, Foster City, CA (US)

( * ) Notice: Subject to any disclaimer, the term of this patent is extended or adjusted under 35 U.S.C. 154(b) by 159 days.

(21) Appl. No.: 10/384,995

(22) Filed: Mar. 10, 2003

(65) Prior Publication Data

US 2004/0178370 A1   Sep. 16, 2004

(51) Int. Cl.[7] .................................................. G01J 3/30
(52) U.S. Cl. .................. 356/317; 356/318; 250/458.1; 250/461.1; 435/6; 435/5
(58) Field of Search ................................ 356/317, 318, 356/417; 250/458.1, 461.1; 435/6, 5, 40.5, 435/34

(56) References Cited

U.S. PATENT DOCUMENTS

| | | |
|---|---|---|
| 5,283,179 A | 2/1994 | Wood |
| 5,578,832 A | 11/1996 | Trulson et al. |
| 5,625,077 A | 4/1997 | Bronstein |
| 5,631,743 A | 5/1997 | Inoue |
| 5,641,641 A | 6/1997 | Wood |
| 5,652,345 A | 7/1997 | Schaap et al. |
| 5,679,803 A | 10/1997 | Bronstein et al. |
| 5,783,381 A | 7/1998 | Bronstein et al. |
| 5,834,758 A | 11/1998 | Trulson et al. |
| 5,925,525 A | 7/1999 | Fodor et al. |
| 5,936,324 A | 8/1999 | Montagu |
| 5,981,956 A | 11/1999 | Stern |
| 6,022,964 A | 2/2000 | Bronstein et al. |
| 6,025,601 A | 2/2000 | Trulson et al. |
| 6,040,138 A | 3/2000 | Lockhart et al. |
| 6,040,193 A | 3/2000 | Winkler et al. |
| 6,124,478 A | 9/2000 | Bronstein et al. |
| 6,133,459 A | 10/2000 | Schaap et al. |
| 6,141,096 A | 10/2000 | Stern et al. |
| 6,160,618 A * | 12/2000 | Garner ....................... 356/318 |
| 6,215,894 B1 | 4/2001 | Zeleny et al. |
| 6,387,675 B1 | 5/2001 | Wood et al. |

(Continued)

FOREIGN PATENT DOCUMENTS

EP   0452905   10/1991

(Continued)

OTHER PUBLICATIONS

International Search Report, PCT/US2004/007103, Int'l Filing Date: Mar. 9, 2004 (6 sheets).

*Primary Examiner*—Layla G. Lauchman
(74) *Attorney, Agent, or Firm*—Harness, Dickey & Pierce, P.L.C.

(57) ABSTRACT

An apparatus for imaging an array of a plurality of features associated with a sample tile. The apparatus includes a stage that supports the sample tile in an illumination region, and an illumination source having a plurality of LEDs adapted to emit light. At least a portion of the light illuminates the illumination region. Additionally, the apparatus includes an image collecting device adapted to selectively collect images of either a first signal when the illumination source is illuminating the illumination region, or a second signal absent illumination of the illumination region. The first signal has wavelengths effectively different from the wavelengths of the portion of the light emitted by the LEDs that illuminates the illumination region.

47 Claims, 5 Drawing Sheets

U.S. PATENT DOCUMENTS

| | | | |
|---|---|---|---|
| 6,252,236 B1 | 6/2001 | Trulson et al. | |
| 6,271,042 B1 | 8/2001 | Watson, Jr. et al. | |
| 6,329,661 B1 | 12/2001 | Perov et al. | |
| 6,403,957 B1 | 6/2002 | Fodor et al. | |
| 6,407,858 B1 | 6/2002 | Montagu | |
| 6,413,722 B1 | 7/2002 | Arnold et al. | |
| 6,471,916 B1 | 10/2002 | Doblett | |
| 6,496,309 B1 | 12/2002 | Bliton et al. | |
| 6,545,264 B1 | 4/2003 | Stern | |
| 6,583,424 B2 | 6/2003 | Staton et al. | |
| 6,597,000 B2 | 7/2003 | Stern | |
| 6,643,076 B2 | 11/2003 | Montagu | |
| 6,646,243 B2 | 11/2003 | Pirrung et al. | |
| 6,720,149 B1 * | 4/2004 | Rava et al. | 435/6 |
| 6,741,344 B1 | 5/2004 | Stern et al. | |
| 6,775,567 B2 * | 8/2004 | Cable et al. | 600/407 |
| 6,794,658 B2 | 9/2004 | MacAulay et al. | |
| 2002/0110828 A1 | 8/2002 | Ferea et al. | |
| 2003/0112432 A1 | 6/2003 | Yguerabide et al. | |
| 2003/0170613 A1 * | 9/2003 | Straus | 435/5 |

FOREIGN PATENT DOCUMENTS

| | | |
|---|---|---|
| WO | WO00/59671 | 10/2000 |
| WO | WO01/63247 | 8/2001 |
| WO | WO02/08754 | 1/2002 |
| WO | WO03/010524 | 2/2003 |

* cited by examiner

COMBINATION READER

FIELD

The invention relates generally to imaging biomolecular or synthetic arrays.

BACKGROUND

Substrate-bound biomolecular or synthetic arrays, such as oligonucleotide arrays, also known as micro arrays, enable the testing of the hybridization of different sequences in a sample to many different probes. These arrays can be composed of hundreds of thousands of probes deposited or synthesized within specific regions, defined as features, on a substrate.

To analyze such arrays, the sample is labeled with one or more detectable markers, such as fluorescent or chemiluminescent makers, that hybridize with the probes at each feature on the substrate. The markers emit luminous signals, for example a fluorescent signal or a chemiluminescent signal, that are imaged and the images are analyzed.

SUMMARY

In various configurations, an apparatus is provided for imaging an array of a plurality of features associated with a sample tile. The apparatus includes a stage that supports the sample tile in an illumination region, and an illumination source having a plurality of LEDs adapted to emit light. At least a portion of the light illuminates the illumination region. Additionally, the apparatus includes an image collecting device adapted to selectively collect images of either a first signal when the illumination source is illuminating the illumination region, or a second signal absent illumination of the illumination region. The first signal has wavelengths effectively different from the wavelengths of the portion of the light emitted by the LEDs that illuminates the illumination region.

Also, in various configurations, a method is provided for collecting images of fluorescent and chemiluminescent signals using an imaging apparatus. The method includes placing a sample tile on a movable stage of the imaging apparatus, wherein the sample tile includes an array of features. At least a portion of the features include at least one hybridized fluorescent marker and/or at least one hybridized chemiluminescent marker. Additionally, the method includes flooding the sample tile with light utilizing an illumination source of the imaging apparatus, thereby exciting the fluorescent marker in the array. The illumination source may include a plurality of LEDs. Furthermore, the method includes collecting images of at least a portion of the array utilizing an image collecting device of the imaging apparatus. The images selectively showing fluorescent signals emitted by the fluorescent markers when the illumination source floods the sample tile with light, and/or a plurality of chemiluminescent signals emitted by the chemiluminescent markers absent the light from the illumination source.

BRIEF DESCRIPTION OF THE DRAWINGS

The present invention will become more fully understood from the detailed description and accompanying drawings, wherein.

DETAILED DESCRIPTION

The following description is merely exemplary in nature and in no way intended to limit the invention, its application, or use.

Figure 1:
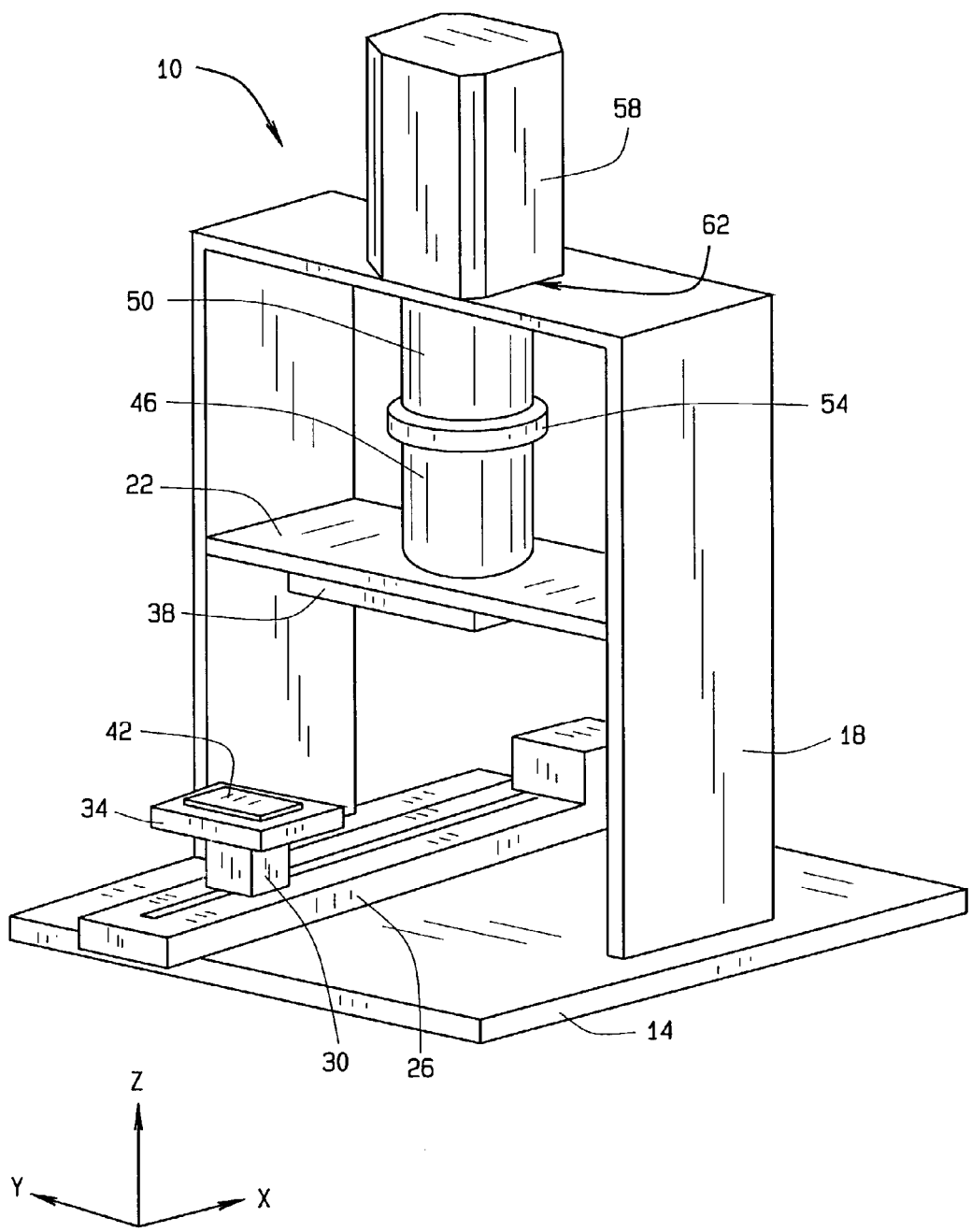
FIG. 1 is a perspective view of an imaging apparatus for collecting images of fluorescent and chemiluminescent hybridized markers in a biomolecular or synthetic sample.

FIG. 1 is a perspective view representative of various configurations of an imaging apparatus 10 for collecting images of fluorescent and chemiluminescent hybridized markers in a biomolecular or synthetic sample. The imaging apparatus 10 includes a base 14, a frame 18 connected to the base 14, and a mid-support 22 coupled to the frame 18. Additionally, the imaging apparatus 10 includes a transport 26 and an elevator 30 that are controlled by a controller (not shown) to orient a stage 34 under an illuminator 38 that illuminates a sample tile 42 positioned on the stage 34. The sample tile 42 is a support, such as glass, ceramic, or plastic, to which at least one feature of a sample (not shown) is associated, i.e. placed, synthesized, or attached. The feature can be, for example, any feature of the sample where a fluorescent and/or chemiluminescent marker has hybridized with a probe attached to the sample tile 42. For example, the feature can be a co-spotted oligonucleotides labeled with one fluorescent marker and one chemiluminescent marker.

In various configurations, the sample tile 42 includes an array of associated features having, for example, hundreds or thousands of features. In some configurations, the sample tile 42 includes a microarray having a larger plurality of associated features, for example, tens of thousands or hundreds of thousands of features. For the sake of convenience and clarity, exemplary configurations will be described below referencing an array of features, but it will be understood that the array could include as few as one feature, or the array could include as many as hundreds of thousands of features, or more.

In various configurations the array of features is a nucleic acid microarray. Such microarrays are becoming an increasingly important tool in bioanalysis and related fields. Nucleic acid microarrays have been developed and find use in a variety of applications, such as gene sequencing, monitoring gene expression, gene mapping, bacterial identification, drug discovery, and combinatorial chemistry. One area in particular in which microarrays find use is in gene expression analysis. Current methods of manufacturing nucleic acid microarrays, and methods of their use is diagnostic assays have been described in U.S. Pat. Nos. 6,413,722, 6,215,894, 6,040,193, 6,040,138, and 6,387,675.

Furthermore, the imaging apparatus 10 in various configurations includes a first lens 46, a second lens 50, a first filter 54, and an image collecting device 58. The first and second lenses 46 and 50 can be any lenses suitable for optical imaging performance, for example medium format photographic lenses. In some configurations not illustrated, a single lens is used for optical imaging performance. In various configurations, the first filter 54 is a longpass filter adapted to pass light having longer wavelengths, for example light having a wavelength greater than about 670 nm., or the first filter 54 is a bandpass filter adapted to pass light having wavelengths included in a certain range of wavelengths, for example light having wavelengths that are between about 670 nm and about 700 nm.

The image collecting device 58 and the second lens 50 are positioned in relation to each other such that a primary imaging surface 62 of image collection device 58 is at the focal plane of the second lens 50. The controller utilizes the transport 26 and the elevator 30 to position the stage 34 such that the tile 42 is at a focal plane of the first lens 46. The transport 26 moves the stage 34 along an x-axis, while the elevator 30 moves the stage 34 along a z-axis. Both the transport 26 and the elevator 30 are controlled by software via the controller, which interfaces with a computer workstation (not shown). Through the workstation, a user enters a command, e.g. "load sample", which is communicated to the controller. The controller interprets the command and utilizes at least one motor (not shown) to move the stage along the x-axis and z-axis to the commanded position. In various configurations the workstation is separate from the imaging apparatus 10. In other various configurations the imaging apparatus 10 includes the workstation. In other various configurations, the imaging apparatus 10 includes various computer workstation components, such as memory and a processor, while other computer workstations components, such as a graphical user interface, are separate from the imaging apparatus 10.

In various configurations, the controller and the transport 26 move the stage 34 to pre-set x-axis positions when loading the tile 42 and imaging the features of the array. For example, in some configurations, the controller is configured to instruct the transport 26 to move the stage 34 to a "loading the sample" position, an "imaging position #1" under illuminator 38, and an "imaging position #2" under the illuminator 38. The elevator 34 is controlled by the controller to position the stage 34 at the focal plane of the first lens 46. The elevator 30 moves the stage 34 along a z-axis, while the first and second lenses 46 and 50 remain stationary to achieve an optimum focus of the array for the image collecting device 58. An algorithm processes image data collected by image collecting device 58 to determine the position for optimum focus of the array. Therefore, an image of the array is auto-focused for the image collecting device 58 without adjusting the first and second lenses 46 and 50.

For example, image collecting device 58 collects imaging data and communicates the data to the workstation where the algorithm determines the clarity of the image. That is, the algorithm analyzes the contrast of the image. If the image does not have a desired contrast, the algorithm instructs the controller to adjust the position of the stage along the z-axis. Then another image is collected and the data is communicated to the workstation where the algorithm again analyzes the contrast. This process is repeated until the contrast is maximized, i.e. an optimum focus is achieved. In various configurations, the fluorescent signals emitted by each fluorescent marker are used by the algorithm to auto-focus the array. In some configurations, the elevator 30 is adapted to rotate the stage 34 in the x-y plane, and the transport 26 is adapted to move the stage 34 along the y-axis.

When the stage 34 is positioned under the illuminator 38, at the focal plane of the first lens 46, the image collecting device 58 collects at least one image of the array of features associated with the tile 42. For example, if the sample tile 42 is in an environment illuminated using the illuminator 38, the image collecting device 58 collects illumination data relating to the intensity of light emitted by the fluorescent marker in each feature. Or, for example, if the sample tile 42 is an environment absent light that will interfere with the chemiluminescent signals, the image collecting device 58 collects illumination data relating to the intensity of light emitted by the chemiluminescent markers in each featurer. The image collecting device 58 can be any device suitable for collecting image data emitted from the array of features. For example, in some configurations, image collecting device 58 is configured to be a CMOS detector array. In some configurations the image collecting device 58 comprises a charge-coupled device (CCD).

Figure 2:
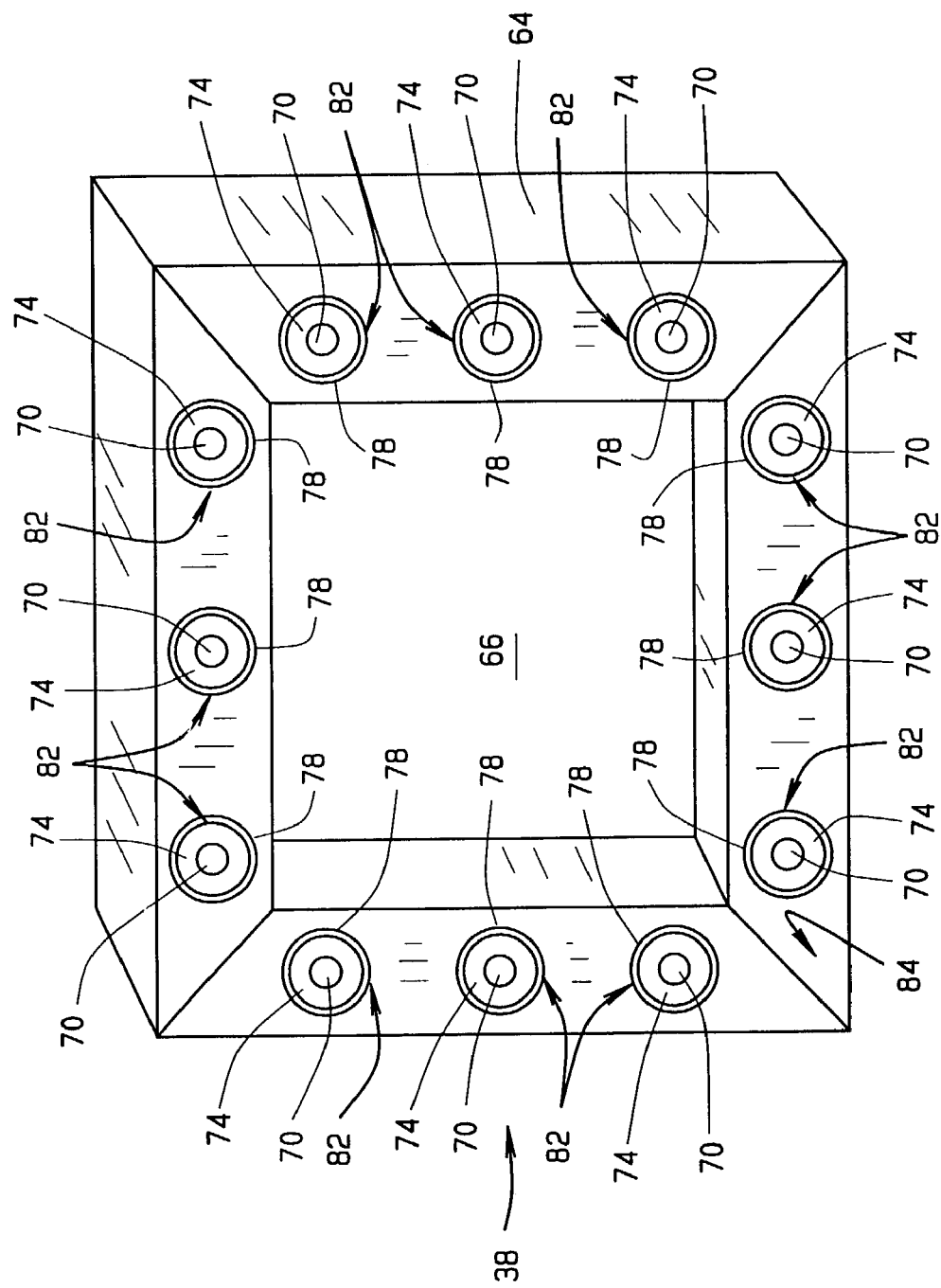
FIG. 2 is a perspective view of an illuminator shown in FIG. 1.

FIG. 2 is a perspective view representative of various configurations of the illuminator 38 (shown in FIG. 1). The illuminator 38 comprises a light source configured to excite the fluorescent marker in each feature by flooding the entire tile 42 (shown in FIG. 1) with light. That is, the illuminator 38 distributes light over the entire tile 42, exciting the fluorescent markers in all features associated with the tile 42 at the same time. Additionally, the illuminator 38 substantially evenly distributes light over the tile 42, such that approximately the same amount of light is distributed over the entire tile 42. The evenly distributed flood illumination provides approximately 360° of light to each feature, thereby allowing more accurate evaluation of the feature by exciting a greater percentage of the fluorescence of each feature, possibly the entire fluorescence of each feature. More specifically, artifacts, i.e. irregularities, in the top surface are less likely to block the excitation light from reaching all areas of the top surface of each feature. Furthermore, flooding the tile and associated array with light from approximately 360° allows a shape and a size of each feature in the array to be easily determined.

In various configurations, the illuminator 38 includes an opening 66 configured to allow images, i.e. fluorescent and/or chemiluminescent light signals, emitted from each feature to pass through the opening 66. The signals are then re-imaged by the first and second lenses 46, 50 (shown in FIG. 1), filtered by the first filter 54 (shown in FIG. 1), and collected by the image collecting device 58 (shown in FIG. 1). Although the illuminator 38 and opening 66 are shown in FIG. 2 as having a rectangular shape, the illuminator 38 and opening 66, in various configurations, can have any geometric shape suitable to flood illuminate the tile 42. In various configurations, for example, the shape of the illuminator 38 matches the shape of the tile 42. For example, in configurations in which the tile 42 is rectangular, the illuminator 38 and opening 66 are also rectangular. In configurations in which the tile 42 is round, the illuminator 38 and opening 66 are likewise round.

Additionally, in various configurations, illuminator 38 can have a continuous ring form, comprising a single continuous body 64 that provides the opening 66, as shown in FIG. 2. Additionally, In various configurations illuminator 38 can have a discontinuous ring form having a plurality of disconnected sections (not shown) that provides the opening 66. For example, illuminator 38 could have discontinuous ring form comprising two disconnected essentially semi-circular sections, or four disconnected straight sections that form a rectangular ring disconnected at the corners.

In various configurations, the illuminator 38 includes a plurality of LEDs 70, wherein each LED 70 is associated with one of a plurality second filters 74 and one of a plurality of diffusers 78. For convenience, the second filters 74 and diffusers 78 are shown in FIG. 2 as having different sizes, but are not required to be of different sizes to practice the invention. In some configurations, second filters 74 and diffusers 78 have the same size and same geometric shape, but in some configurations, the second filters 74 and diffusers 78 have different sizes and geometric shapes. Each LED 70 is enclosed in one of a plurality of recesses 82 that are covered by second filters 74 and diffusers 78. However, in some configurations, illuminator 38 includes a plurality of any suitable excitation light sources other than LEDs 70, for example, tungsten or xenon bulbs, a laser light source, and/or a fiber optic light source.

The LEDs 70 are configured to emit a wavelength of light at an intensity level that excites a fluorescent marker in each feature. For example, in some configurations, the illuminator 38 includes LEDs 70 that emit light having a wavelength of about 635 nm to excite fluorescent markers that emit red light. In some configurations, the illuminator 38 includes LEDs 70 that emit light having a wavelength of about 470 nm used to excite fluorescent markers that emit blue light. Other wavelengths may be used to excite fluorescent markers having other excitation requirements. In various configurations the Illuminator 38 includes LEDs 70 that emit light having various wavelengths. For example, various LEDs 70 emit light having a wavelength of 635 nm, while other LEDs 70 in illuminator 38 emit light having a wavelength of 470 nm, and other LEDs 70 may emit light having other wavelengths. This would allow the use of multi-color fluorescent markers in the array of features.

In various configurations, imaging apparatus 10 is configured to allow the illuminator 38 to be removed and replaced with an illuminator 38 comprising LEDs that emit light having a different wavelength. Thus, if tile 42 associated with an array of features having fluorescent markers that emit red light is removed and replaced with a tile 42 associated with an array of features having fluorescent markers that emit blue light, the illuminator 38 can be removed and replaced accordingly.

Furthermore, in some configurations, each of the LEDs 70 is oriented in the recesses 82 so that light provided by each LED 70 is directed toward one or more desired areas of the tile 42. For example, each LED 70 can be oriented so that light emitted from each LED is generally directed to the center of the tile 42, or each LED 70 can be oriented so that light emitted from each LED is directed to different sections of the tile 42. In various configurations, a front face 84 of the illuminator 38 is angled inward to allow the LEDs 70 to point downward and slightly inward toward a focal point in the center of the tile 42.

In some configurations, the diffusers 78 diffuse light emitted from each LED 70 to substantially evenly distribute the light from each LED 70 over the entire tile 42. That is, diffusers 78 have a divergence angle selected so that light emitted from each LED 70 illuminates the entire tile 42. Therefore, the light emitted from each LED 70 overlaps with the light emitted from each of the other LEDs 70. Thus, the intensity of light provided by the illuminator 38, over the entire tile 42 is a function of the number of LEDs included in the illuminator 38 and the selected intensity of the LEDs 70. In some configurations, a single diffuser (not shown) is used. In various configurations the single diffuser has the same shape as the front face 84 of illuminator 38. The single diffuser covers each LED 70 and simultaneously diffuses the light emitted from each LED 70. In various other configurations at least two diffusers (not shown) are used to diffuse light emitted by the LEDs 70.

The second filters 74 eliminate light emitted by the LEDs 70 having a wavelength that would reflect off the array, the tile 42, or the stage 38 and undesirably pass through the first filter 54 to the image collecting device 58. For example, in some configurations, the first filter 54 passes light having a wavelength greater than about 640 nm, and the second filter 74 passes only light having a wavelength of less than about 635 nm. In some configurations, the second filters 74 are shortpass filters adapted to pass light having shorter wavelengths, for example light having a wavelength less than about 635 nm. In some configurations, the second filter 74 is a bandpass filter adapted to pass light having wavelengths included in a certain range of wavelengths, for example light having wavelengths that are between about 550 nm and about 635 nm. In various configurations, the apparatus 10 includes a single second filter (not shown for eliminating light emitted by the LEDs 70. In various other configurations, the apparatus 10 includes two or more second filters (not shown), whereby each of the second filters 74 filters light emitted by at least one of the LEDs 70.

In various configurations, EPI illumination is utilized, in place of the illuminator 38, to illuminate the array and excite the fluorescent markers. An EPI based system would have a dichroic beam splitter (not shown) between the first lens 46 and the first filter 54. Light emitted from the EPI illuminator would be shaped and imaged onto the sample tile 42 through the first lens 46. Leds, a lamp or a laser could be used as the illumination source. Any suitable illumination source can be utilized to illuminate the array and excite the fluorescent markers. For example, off axis illumination and electro luminescent panels can be utilized.

Referring to FIG. 1, the first filter 54 is positioned between the first lens 46 and the second lens 50 when it is desirable to filter out light reflecting off the array from the illuminator 38 having certain wavelengths. Therefore, light emitted from the illuminator 38 that overlaps with the fluorescent emissions of the array of features is separated from the fluorescent emissions and substantially prevented from reaching the image collecting device 58. The first filter 54 can be removed when filtering is not desired, for example, when chemiluminescent emissions are to be imaged all light the can interfere with the enzymatically generated chemiluminescent signals must be substantially removed from the environment surrounding the imaging apparatus 10. In some configurations, the removal and insertion of the first filter 54 is automated by the controller and a mechanism (not shown) suitable for inserting the first filter 54 between the first and second lenses 46 and 50, and removing the first filter 46 when desired.

In some configurations, a filter wheel having a plurality of filters is used as a first filter 54, wherein each filter of the filter wheel filters out light of a different wavelength, or within a different bandwidth. Positioning of the filter wheel is automated by the controller and a mechanism suitable to rotate the wheel such that a desired filter, or no filter, is positioned between the first and second lenses 46 and 50. The first filter 54 works in combination with the second filter 78 to allow only fluorescent emissions of the array to be collected by the image collecting device 58 when the illuminator 38 is illuminated.

Figure 3:
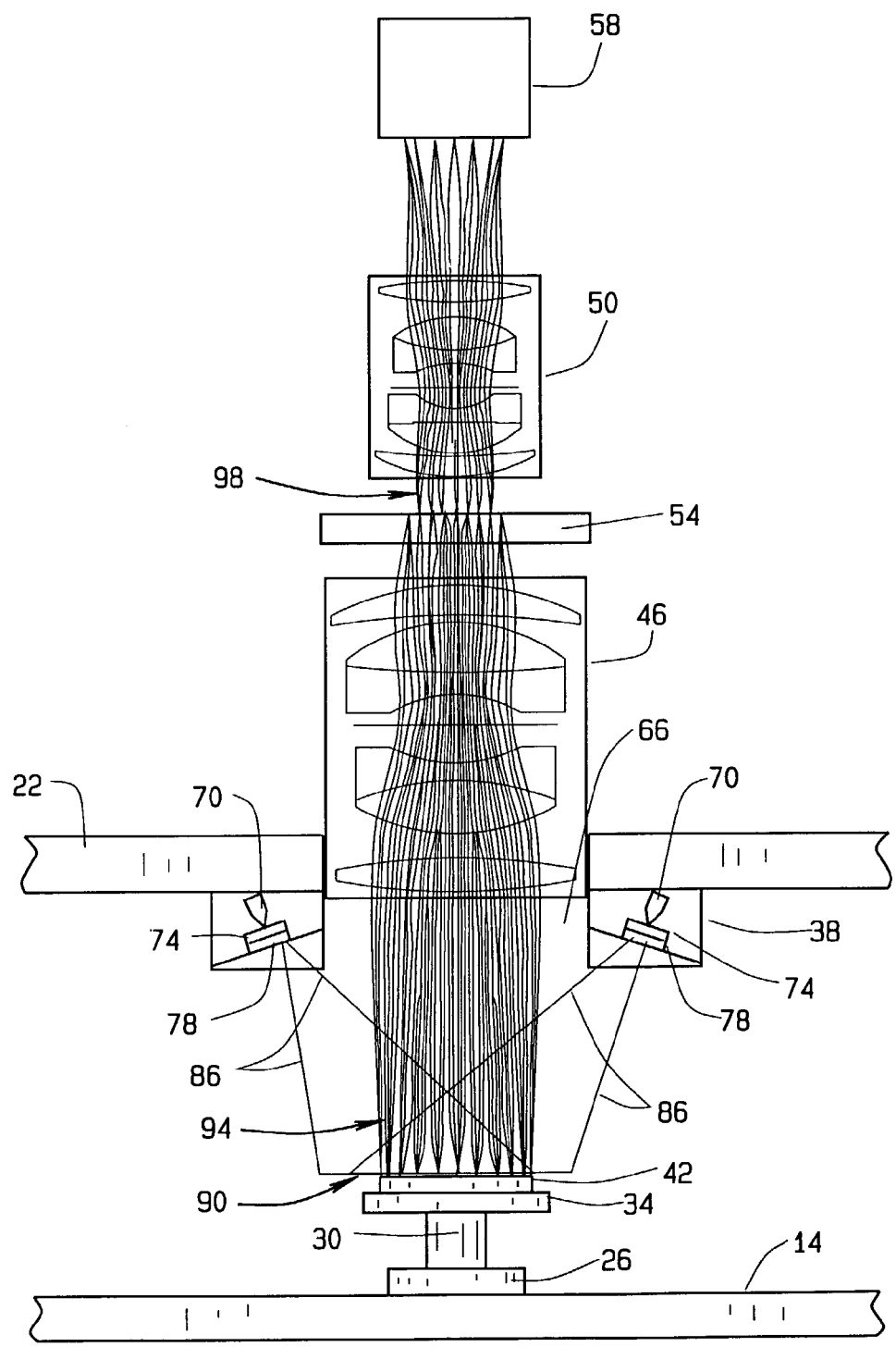
FIG. 3 is schematic of a cross-section of the imaging apparatus shown in FIG. 1, illustrating illumination patterns of the illuminator shown in FIG. 2.

FIG. 3 is a schematic of a cross-section of various configurations of the imaging apparatus 10 (shown in FIG. 1), illustrating the flood illumination of the illuminator 38 (shown in FIG. 2) and the path of the fluorescent signals emitted from an array of features. Each LED 70 emits light directed at the tile 42 and the associated array. The light emitted by each LED 70 is filtered by the second filter 78 so that only light having a desired wavelength, or within a desired range of wavelengths, illuminates the tile 42 and associated array. Additionally, light emitted from each LED 70 is diffused by the diffuser 78 to provide a substantially uniform intensity of light over the entire tile 42, as indicated by LED illumination pattern lines 86. Therefore, the light emitted from each LED 70 overlaps with the light emitted from at least one of the other LEDs 70, as generally indicated at overlap area 90.

The light emitted by the LEDs 70, filtered by the second filters 74, and diffused by the diffusers 78, excites the fluorescent markers in each feature of the array, resulting the emission of fluorescent signals 94. The fluorescent signals 94 pass through the opening 66 in the illuminator 38 and enter the first lens 46, where they are re-imaged. The signals 94 are then filtered by the first filter 54, which filters out any light from the LEDs 70 that has reflected off of the array of features, the tile 42 and/or the stage 34. The filtered signals 98 then pass through the second lens 50 where they are re-imaged again. After passing through the second lens 50, the fluorescent signals 94 are collected by image collecting device 58, and the collected image data is transmitted to a computer based system (not shown), where the data is processed and analyzed.

Figure 4:
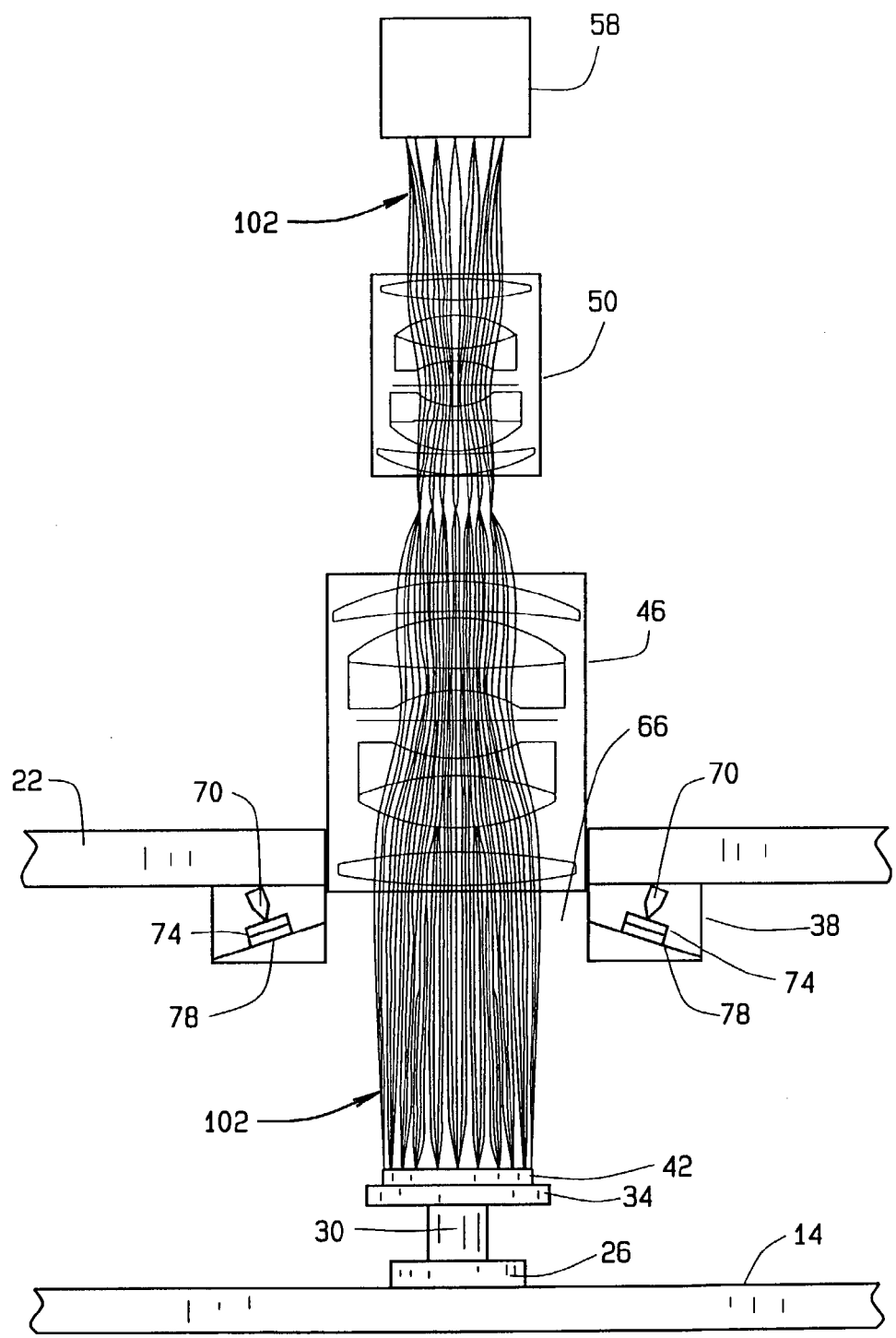
FIG. 4 is a schematic of a cross-section of the imaging apparatus shown in FIG. 1, illustrating the path of the chemiluminescent signals emitted from an array of features.

FIG. 4 is a schematic of a cross-section representative of various configurations of imaging apparatus 10 (shown in FIG. 1), illustrating the path of the chemiluminescent signals emitted from an array of features. To collect images of chemiluminescent signals 102 emitted by the feature in the array, the first filter 54 (shown in FIG. 3) is removed from between the first and second lenses 46 and 50, and the illuminator 38 is turned off. The chemiluminescent signals must be imaged in a substantially light free environment. That is, an environment substantially free from any light that will interfere with the chemiluminescent signals emitted from the array.

In various configurations the chemiluminescent signals are enzymatically generated. Methods for generating chemiluminescent signal in biomolecular array, for example nucleic acid microarrays, have been described in U.S. Pat. Nos. 5,625,077, 5,652,345, 5,679,803, 5,783,381, 6,022,964, 6,133,459, and 6,124,478.

The chemiluminescent signals 102 emitted from the array pass through the first and second lenses 46 and 50, where the chemiluminescent signals 102 are re-imaged by each lenses 46 and 50. After passing through the lenses 46 and 50, the chemiluminescent signals 102 are collected by image collecting device 58. The collected image data is then transmitted to the computer based system, where the data is processed and analyzed. In various configurations, each feature may have more than one chemiluminescent marker hybridized with probes associated with the tile 42. In which case, the first filter 54 would not be removed in order to filter out light emitted from one of the chemiluminescent markers of the features while allowing wavelengths of different chemiluminescent signals to pass and be imaged by the image collecting device 58. The first filter 54 would then be removed and replaced with a different first filter 54 that would allow other chemiluminescent signals to be imaged.

Referring now to both FIGS. 3 and 4, in various configurations, the filtered fluorescent signals 98 collected by image collecting device 58 are used to auto-focus the array of features for the image collecting device 58, as described above in reference to FIG. 1, for example corrections for chromatic aberrations are made. Additionally, the filtered fluorescent signals 98 collected by image collecting device 58 are used for gridding the array of features. That is, the filtered fluorescent signals 98 are used to identify the location of each feature within the array. Furthermore, the filtered fluorescent signals 98 collected by image collecting device 58 are used to normalize the array. More specifically, the filtered fluorescent signals 98 are used to normalize the chemiluminescent signals 102 collected by the image collecting device 58.

Figure 5:
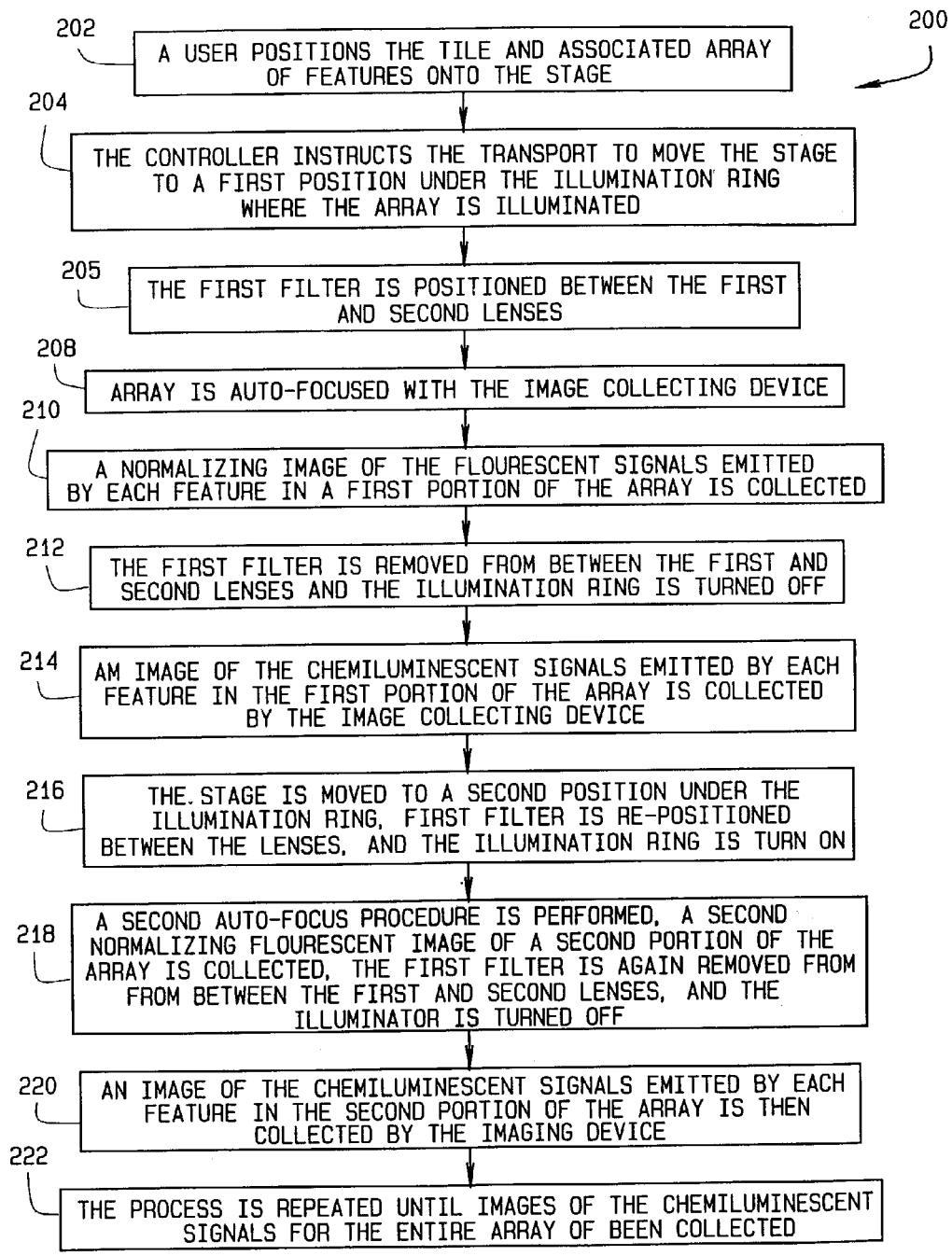
FIG. 5 is a flow chart for the basic operation of the imaging apparatus shown in FIG. 1.

FIG. 5 is a flow chart 200 representative of various method configurations for operating an imaging apparatus 10 for imaging an array of features. To begin, a user positions the tile 42 and associated array of features onto the stage 34, as indicated at 202. The controller instructs the transport 26 to move the stage 34 along the x-axis to a first position under the illuminator 38, where the array is illuminated by the illuminator 38, as indicated at 204. Next the first filter 54 is positioned between the first and second lenses 46 and 50, as indicated at 206. The array is then auto-focused for the image collecting device 58 by moving the stage 34 along the z-axis, via the elevator 30, as indicated at 208. A normalizing image of the fluorescent signals 98 emitted by each feature in a first portion of the array is then collected, as indicated at 210. Next, the first filter 54 is removed from between the first and second lenses 46 and 50, and the illuminator 38 is turned off, as indicated at 212, thereby providing a substantially light free environment for imaging the chemiluminescent signals emitted by each feature. Then an image of the chemiluminescent signals 102 emitted by each feature in the first portion of the array is collected by the image collecting device 58, as indicated at 214.

Next, in various configurations, depending on the size of the array, the stage 30 is moved to a second position under the illuminator 38, first filter 54 is re-positioned between the lenses 46 and 50, and the illuminator 38 is turned on, as indicated at 216. Then, a second auto-focus procedure is performed, a normalizing fluorescent image of a second portion of the array is collected, the first filter 54 is again removed from between the first and second lenses 46 and 50, and illuminator 38 is again turned off, as indicated at 218. An image of the chemiluminescent signals 102 emitted by each feature in the second portion of the array is then collected by the imaging device 58, as indicated at 220. This process is repeated, as needed, until images of the chemiluminescent signals 102 for the entire array have been collected, as indicated at 222.

Thus, the imaging apparatus of the present invention automatically acquires multiple images of an array of fluorescent/chemiluminescent co-hybridized features, thereby acquiring image data for the entire array using a single apparatus. Additionally, the present invention allows better alignment between the fluorescent and the chemiluminescent image data because the optics are the same for the collection in both channels. Furthermore, the illuminator substantially evenly distributes excitation light over the entire array, thereby providing more consistent image data for multiple images across the entire array.

While the invention has been described in terms of various configurations, those skilled in the art will recognize that the invention can be practiced with modification within the spirit and scope of the claims.

What is claimed is:

1. A method for collecting images of fluorescent and chemiluminescent signals using an imaging apparatus, the method comprising:

placing a sample tile on a stage of the imaging apparatus, the sample tile having an array associated therewith, the array including a plurality of features, wherein at least a portion of the features includes at least one of a fluorescent marker and a chemiluminescent marker;

flooding an entirety of the sample tile with light utilizing an illuminator of the imaging apparatus, the illuminator including a plurality of LEDs, thereby exciting the fluorescent markers in the array; and collecting images of at least a portion of the array utilizing an image collecting device of the imaging apparatus, the images selectively showing fluorescent signals emitted by the fluorescent markers when the illuminator floods the array with light and chemiluminescent signals emitted by the chemiluminescent markers absent light from the illuminator.

2. The method of claim 1 wherein placing the tile on the stage comprises:

placing the tile on a movable stage; and automatically positioning the stage in relation to a lens such that images of multiple portions of the array of features are collectible by the image collection device.

3. The method of claim 2, wherein placing the sample tile on the movable stage comprises auto-focusing the sample tile for the image collecting device by automatically positioning the stage at a distance from a lens such that the lens directs a focused image to the collection device.

4. The method of claim 1, wherein flooding the sample tile with light comprises associating one of a plurality of filters with each LED, whereby each filter filters the light emitted by the associated LED such that light, other than light having wavelengths suitable to excite the fluorescent markers of the array is effectively prevented from passing through each filter.

5. The method of claim 1, wherein flooding the sample tile with light comprises positioning a filter between the stage and the LEDs, whereby the filter filters the light emitted by the LEDs such that light, other than light having wavelengths suitable to excite the fluorescent markers of the array is effectively prevented from passing through the filter.

6. The method of claim 1, wherein flooding the sample tile with light comprises:

associating one of a plurality of diffusers with each LED; and diffusing the light emitted from each LED utilizing the diffusers such that the light emitted from each LED overlaps the light emitted from at least one other LED at a top surface of the sample tile, thereby flooding the sample tile with light from a plurality of directions such that at least one of a shape and a size of at least a portion of the features is determinable.

7. The method of claim 1, wherein collecting images comprises positioning a filter between the stage and the image collecting device, the filter adapted to effectively prevent light, other than a fluorescent signal emitted by each fluorescent marker from passing through the filter.

8. The method of claim 1, wherein collecting images comprises:

exciting the fluorescent markers in the array using the light emitted from the illuminator;

collecting an image of the fluorescent signals emitted from the array;

disabling the light emitted by the illuminator; and collecting an image of the chemiluminescent signals emitted from the array.

9. A method for collecting images of fluorescent and chemiluminescent signals emitted from a plurality of features grouped as an array, the method comprising:

a. positioning the array on a stage connected to an elevator of an imaging system;

b. automatically moving the array to a first position under a lens of the imaging system using a transport connected to the elevator;

c. positioning a first filter between the stage and an image collecting device of the imaging system;

d. auto-focusing the image collecting device by using the elevator to position the array at a focal plane of the lens;

e. flooding light over the array from a plurality of directions using an illuminator, thereby resulting in at least some of the features emitting a fluorescent signal;

f. imaging the fluorescent signals emitted from a first portion of the array using the image collecting device;

g. imaging chemiluminescent signals emitted from at least a portion of the feature in the first portion of the array using the image collecting device;

h. automatically moving the array to a second position under the lens; and i. repeating c, d, e, f, and g for the second portion of the array.

10. The method of claim 9, wherein positioning the first filter between the stage and the image collecting device, comprises configuring the first filter such that light, other than the fluorescent signals is effectively prevented from passing through the first filter.

11. The method of claim 9, wherein flooding light over the array comprises:

using an illuminator including a plurality of LEDs; and associating one of a plurality of second filters with each LED in the illuminator, whereby each second filter filters the light emitted by the associated LED such that light other than light having wavelengths suitable to result in the emission of the fluorescent signals, is effectively prevented from passing through each second filter.

12. The method of claim 11, wherein imaging the chemiluminescent signals comprises removing the first filter from between the stage and the image collecting device, thereby allowing the image collecting device to image the chemiluminescent signals.

13. An imaging system for automatically collecting multiple images of an array associated with a sample tile, the array including a plurality of features, the system comprising:

an automated stage movable along an x-axis, wherein the stage is configured to support the sample tile;

an illuminator configured to emit light from at least two directions at the sample tile thereby exciting a fluorescent marker included in each of at least some of the features in the array, wherein the illuminator is positioned such that the array is between the illuminator and the stage; and an image collecting device configured to collect multiple images of the array, wherein the images selectively include one of a plurality of fluorescent signals emitted by the excited fluorescent markers, and a plurality of chemiluminescent signals emitted by a chemiluminescent marker included in at least some of the features.

14. The system of claim 13, wherein the automated stage is configured to move along the x-axis to a first position under a lens associated with the image collecting device, thereby enabling the image collecting device to collect a first image including the fluorescent signals emitted from the features included in a first portion of the array, and a second image including the chemiluminescent signals emitted from the features included in the first portion of the array.

15. The system of claim 14, wherein the automated stage is configured to move along the x-axis to a second position under the lens, thereby enabling the image collecting device to collect a third image including the fluorescent signals emitted from features included in a second portion of the array, and a fourth image including the chemiluminescent signals emitted from the features included in the second portion of the array.

16. The system of claim 14, wherein the automated stage is further movable along a z-axis to automatically position the stage at a focal plane of the lens.

17. The system of claim 13, wherein the illuminator includes a plurality of LEDs configured to emit light having wavelengths suitable to excite the fluorescent markers in the array.

18. The system of claim 17, wherein the illuminator further includes a plurality of filters, wherein each filter is associated with one of the LEDs, each filter is configured to filter the light emitted by the corresponding LED such that light, other than light having wavelengths suitable to excite the fluorescent markers, is effectively prevented from passing through each filter.

19. The system of claim 17, wherein the illuminator further includes a filter positioned between the stage and the LEDs, whereby the filter is configured to filter the light emitted by the LEDs such that light, other than light having wavelengths suitable to excite the fluorescent markers, is effectively prevented from passing through the filter.

20. The system of claim 17, wherein the illuminator further includes a plurality of diffusers configured to diffuse the light emitted from each LED such that the light emitted from each LED overlaps the light emitted from at least one other LED at a top surface of the stage, thereby flooding the array with light from a plurality of directions so that at least one of a shape and a size of at least one feature is determinable.

21. The system of claim 13, wherein the illuminator comprises an illumination ring having a single continuous body that forms a ring with an opening therethrough.

22. An apparatus for automatically collecting multiple images of an array associated with a sample tile, the array including a plurality of features, the apparatus comprising:
a movable stage configured to support the sample tile, wherein at least a portion of the features include at least one of a fluorescent marker and a chemiluminescent marker;
an illuminator configured to provide light for illuminating the array, wherein the illuminator includes a plurality of diffusers configured to diffuse the light emitted from the illuminator such that array is flooded with light from a plurality of directions so that at least one of a shape and a size of at least one feature is determinable; and
a charge-coupled device (CCD) configured to collect multiple images, wherein the images include at least one of:
a plurality of fluorescent signals emitted by the fluorescent markers, and
a plurality of chemiluminescent signals emitted by the chemiluminescent markers.

23. The apparatus of claim 22, wherein the illuminator further includes a plurality of LEDs configured to emit the light provided by the illuminator, wherein each LED is associated with one of the diffusers, such that the light emitted from each LED overlaps the light emitted from at least one other LED at a top surface of the array, thereby flooding the array with light.

24. The apparatus of claim 23, wherein the illuminator is positioned such that the array is between the illuminator and the stage, and each LED is configured to emit light having wavelengths suitable to excite the fluorescent markers in the array.

25. The apparatus of claim 24, wherein the illuminator further includes a plurality of filters, wherein each filter is associated with one of the LEDs, each filter is configured to filter the light emitted by the corresponding LED such that light, other than light having wavelengths suitable to excite the fluorescent markers, is effectively prevented from passing through each filter.

26. The apparatus of claim 22, wherein the stage is further configured to move along an x-axis to a first position under a lens associated with the CCD, thereby enabling the CCD to collect a first image including a plurality of fluorescent signals emitted by the excited fluorescent markers of features included in a first portion of the array, and a second image including a plurality of chemiluminescent signals emitted from the chemiluminescent markers of the features included in the first portion of the array.

27. The apparatus of claim 26, wherein the stage is further configured to move along the x-axis to a second position under the lens, thereby enabling the CCD to collect a third image including the fluorescent signals emitted from features included in a second portion of the array, and a fourth image including the chemiluminescent signals emitted from the features included in the second portion of the array.

28. The apparatus of claim 26, wherein the stage is further configured to move along a z-axis to position the stage at a focal plane of the lens.

29. The apparatus of claim 26, wherein the stage is further configured to move along a y-axis.

30. A method for collecting images of fluorescent and chemiluminescent signals emitted from a plurality of features grouped as an array, the method comprising:
positioning the array within an imaging region;
illuminating the imaging region;
imaging the fluorescent signals while the array is within the imaging region; and
imaging the chemiluminescent signals while the array is within the imaging region, absent the illumination
wherein illuminating the array comprises flooding the array with light from a plurality of directions.

31. The method of claim 30, wherein positioning the array comprises positioning the array at a first position within the imaging region.

32. The method of claim 31, wherein imaging the fluorescent signals comprises imaging the fluorescent signals while the array is at the first position.

33. The method of claim 32, wherein imaging the chemiluminescent signals comprises imaging the chemiluminescent signals while the array is at the first position.

34. The method of claim 33, wherein positioning the array further comprises positioning the array at a second position within the imaging region.

35. The method of claim 34, wherein imaging the fluorescent signals further comprises imaging the fluorescent signals while the array is at the second position.

36. The method of claim 35, wherein imaging the chemiluminescent signals further comprises imaging the chemiluminescent signals while the array is at the second position.

37. The method of claim 30, further comprising collecting at least one of the fluorescent signals and the chemiluminescent signals.

38. An imaging apparatus for imaging fluorescent and chemiluminescent signals, the apparatus comprising:
a stage configured to support a tile within an imaging region, the tile having at least one feature thereon including at least one fluorescent marker and at least one chemiluminescent marker;

an illumination source configured to illuminate the imaging region with light from a plurality of directions; and an imaging device configured to selectively collect a plurality of images of the feature while the tile is within the imaging region, the images including at least one image of a fluorescent signal emitted from the fluorescent marker and at least one image of a chemiluminescent signal emitted from the chemiluminescent marker.

39. The imaging apparatus of claim 38, wherein the tile is constructed of a material selected from the group consisting of glass, ceramic, and plastic.

40. The imaging apparatus of claim 38, wherein the illumination source comprises an illumination source having a frame defining an opening through which the fluorescent and chemiluminescent signals pass.

41. The imaging apparatus of claim 40, wherein the illumination source further includes a plurality of LEDs configured to flood light on the imaging region.

42. The imaging apparatus of claim 38, wherein the illumination source is one of:
   at least one LED;
   at least one tungsten light bulb;
   at least one xenon light bulb;
   at least one laser light source; and
   at least one fiber optic light source.

43. The imaging apparatus of claim 38, wherein the tile has a plurality of features arranged in an array thereon, each feature including at least one fluorescent marker and at least one chemiluminescent marker.

44. The imaging apparatus of claim 43, wherein the stage is further configured to be movable to a first position such that the plurality of images collected by the imaging device includes at least one image of fluorescent signals emitted from the fluorescent markers of a first portion of the array and at least one image of chemiluminescent signals emitted from the chemiluminescent markers of the first portion of the array.

45. The imaging apparatus of claim 44, wherein the stage is further configured to be movable to a second position such that the plurality of images collected by the imaging device further includes at least one image of fluorescent signals emitted from the fluorescent markers of a second portion of the array and at least one image of chemiluminescent signals emitted from the chemiluminescent markers of the second portion of the array.

46. The imaging apparatus of claim 38, wherein the stage is further configured to be movable along at least one of an x-axis, a y-axis, and a z-axis.

47. The imaging apparatus of claim 38, wherein the imaging device comprises one of a complementary metal oxide semiconductor (CMOS) detector array and a charge-coupled device (CCD).

* * * * *